(12) United States Patent
Ikegami et al.

(10) Patent No.: US 10,354,385 B2
(45) Date of Patent: Jul. 16, 2019

(54) OPTICAL COHERENCE TOMOGRAPHY (OCT) DATA PROCESSING METHOD, STORAGE MEDIUM STORING PROGRAM FOR EXECUTING THE OCT DATA PROCESSING METHOD, AND PROCESSING DEVICE

(71) Applicant: CANON KABUSHIKI KAISHA, Tokyo (JP)

(72) Inventors: Tomoyuki Ikegami, Hiratsuka (JP); Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/000,328

(22) Filed: Jun. 5, 2018

(65) Prior Publication Data

US 2018/0350076 A1    Dec. 6, 2018

Related U.S. Application Data

(62) Division of application No. 15/441,884, filed on Feb. 24, 2017, now Pat. No. 10,007,989.

(30) Foreign Application Priority Data

Mar. 8, 2016 (JP) ................. 2016-044253

(51) Int. Cl.
*A61B 3/00* (2006.01)
*G06T 7/00* (2017.01)
(Continued)

(52) U.S. Cl.
CPC .......... *G06T 7/0016* (2013.01); *A61B 3/0025* (2013.01); *A61B 3/0058* (2013.01); *A61B 3/102* (2013.01); *A61B 3/1233* (2013.01); *G06T 7/12* (2017.01); *G06T 7/248* (2017.01); *G06T 7/60* (2013.01); *G06T 7/70* (2017.01); *G06T 15/08* (2013.01); *G06T 15/10* (2013.01); *G06T 2207/10016* (2013.01); *G06T 2207/10101* (2013.01); *G06T 2207/30101* (2013.01); *G06T 2207/30104* (2013.01); *G06T 2207/30204* (2013.01); *G06T 2211/404* (2013.01)

(58) Field of Classification Search
CPC .................................. G06T 7/00; A61B 3/00
USPC ......................................................... 382/103
See application file for complete search history.

(56) References Cited

U.S. PATENT DOCUMENTS

| | | | | |
|---|---|---|---|---|
| 9,795,291 | B2 * | 10/2017 | Satake | ................. A61B 3/1225 |
| 10,007,989 | B2 * | 6/2018 | Ikegami | .................. G06T 7/248 |
| 2014/0221827 | A1 | 8/2014 | Motaghiannezam et al. | |

OTHER PUBLICATIONS

Jeff Fingler, et al., "Mobility and transverse flow visualization using phase variance contrast with spectral domain optical coherence tomography," Optics Express, vol. 15, No. 20, 2007, pp. 12636-12653.

(Continued)

*Primary Examiner* — Abolfazl Tabatabai
(74) *Attorney, Agent, or Firm* — Venable LLP

(57) ABSTRACT

An Optical Coherence Tomography (OCT) data processing apparatus includes an acquisition unit configured to acquire three dimensional (3-D) OCT data of an object to be inspected, a generation unit configured to generate a motion contrast image based on the 3-D OCT data, and a detection unit configured to detect a inner surface coordinate of a vessel wall based on position information of an edge of a vessel region in the motion contrast image.

12 Claims, 8 Drawing Sheets

(51) Int. Cl.
    *G06T 7/246*    (2017.01)
    *G06T 7/70*     (2017.01)
    *A61B 3/10*     (2006.01)
    *A61B 3/12*     (2006.01)
    *G06T 7/60*     (2017.01)
    *G06T 15/08*    (2011.01)
    *G06T 15/10*    (2011.01)
    *G06T 7/12*     (2017.01)
    *A61B 6/00*     (2006.01)

(56)                References Cited

OTHER PUBLICATIONS

Adrian Mariampillai, et al., "Speckle variance detection of microvasculature using swept-source optical coherence tomography," Optics Letters, vol. 33, No. 13, 2008, pp. 1530-1532.
Adrian Mariampillai, et al., "Optimized speckle variance OCT imaging of microvasculature," Optics Letters, vol. 35, No. 8, 2010, pp. 1257-1259.
Copending, unpublished U.S. Appl. No. 15/408,867, filed Jan. 18, 2017, to Isao Komine, et al.

* cited by examiner

OPTICAL COHERENCE TOMOGRAPHY (OCT) DATA PROCESSING METHOD, STORAGE MEDIUM STORING PROGRAM FOR EXECUTING THE OCT DATA PROCESSING METHOD, AND PROCESSING DEVICE

This application is a divisional application of U.S. patent application Ser. No. 15/441,884, filed Feb. 24, 2017, which claims benefit to Japanese Patent Application No. 2016-044253, filed on Mar. 8, 2016, which are hereby incorporated by reference herein in their entireties.

BACKGROUND

Field of the Invention

The present disclosure relates to an Optical Coherence Tomography (OCT) data processing method for OCT data acquired by optical coherence tomography, a storage medium storing a program for executing the OCT data processing method, and a processing device.

Description of the Related Art

As a method of acquiring a tomographic image of an object to be inspected, for example, a living body, in a non-destructive and a non-invasive manner, optical coherence tomography has been put into practical use. An OCT apparatus for executing the above-mentioned method, which is capable of acquiring a tomographic image of an object to be inspected, for example, a retina in a fundus of an eye, is widely used for ophthalmologic diagnosis of the retina, or the like.

The OCT apparatus is configured to cause light reflected from the object to be inspected and reference light to interfere with each other, and to analyze time dependence or wavenumber dependence of an intensity of the interference light, to thereby acquire a tomographic image. As such uan OCT apparatus, there are known a time domain optical coherence tomography (TD-OCT) apparatus, a spectral domain optical coherence tomography (SD-OCT) apparatus, and a swept-source optical coherence tomography (SS-OCT) apparatus. The TD-OCT apparatus is configured to acquire depth information on the object to be inspected by changing an optical path length of the reference light by moving a reference mirror. The SD-OCT apparatus is configured to acquire the depth information by using light emitted from a broadband light source. The SS-OCT apparatus is configured to acquire the depth information by using light emitted from a wavelength-tunable light source capable of changing an oscillation wavelength. The SD-OCT apparatus and the SS-OCT apparatus are collectively referred to as "Fourier domain optical coherence tomography (FD-OCT) apparatus".

In recent years, there has been proposed simulated angiography using the FD-OCT apparatus, which is referred to as "OCT angiography (OCTA)". In fluorescence angiography, which is general angiography in contemporary clinical medicine, injection of a fluorescent dye (for example, fluorescein or indocyanine green) into a body is required. A bright region through which the fluorescent dye passes is imaged, to thereby display a vessel two-dimensionally. However, a contrast medium may produce side effects including nausea, eruption, and coughing, and may cause shock symptoms on rare occasions. Hence, angiography involves some risks. Meanwhile, OCTA enables non-invasive simulated angiography without a risk of injecting a foreign matter into the body, and enables three-dimensional display of a network of vessels. In addition, OCTA is attracting attention because OCTA is higher in resolution than fluorescence angiography and can visualize minute vessels or blood flow of the fundus.

As OCTA, there are proposed a plurality of methods depending on a difference in manner of detecting a vessel region. For example, Fingler et al. "Mobility and transverse flow visualization using phase variance contrast with spectral domain optical coherence tomography" Optics Express. Vol. 15, No. 20. pp. 12636-12653 (2007), proposes a method of extracting only signals with time modulation from interference signals acquired by the OCT apparatus, to thereby separate the interference signals caused by the blood flow. There are also proposed a method utilizing phase fluctuations due to the blood flow ("Speckle variance detection of microvasculature using swept-source optical coherence tomography" Optics Letters Vol. 33, No. 13, pp. 1530-1532 (2008)), a method utilizing intensity fluctuations due to the blood flow (Mariampillai et al., "Optimized speckle variance OCT imaging of microvasculature," Optics Letters Vol. 35, No. 8, pp. 1257-1259 (2010) or U.S. Patent Application Publication No. 2014/221827), and the like.

Currently, in medical sites, an examination of hypertension, or the like, places an importance on observation of a change in hypertrophy of the vessel, which leads to arteriosclerosis, and there is a demand to acquire information relating to the hypertrophy of the vessel, that is, information on a vessel wall by a simple method.

SUMMARY

The present disclosure has been made in order to meet the above-mentioned demand, and has an object to provide an OCT data processing method capable of acquiring information relating to a vessel wall by using OCTA in a simplified manner, a storage medium storing a program for executing the OCT data processing method, and a processing device.

In order to solve the above-mentioned problem, according to one embodiment, the present disclosure provides an OCT data processing method, including a signal acquiring step of acquiring interference signal sets of a plurality of frames including interference signal sets corresponding to a plurality of frames that form an image of the same cross section of an object to be inspected, generating three-dimensional (3-D) tomographic image data on the object to be inspected from the interference signal sets of the plurality of frames, generating 3-D motion contrast data based on a pixel with time modulation in the object to be inspected from the interference signal sets corresponding to the plurality of frames that form the same cross section, extracting a vessel from the object to be inspected based on one of the 3-D tomographic image data and the 3-D motion contrast data, detecting a coordinate of an outer surface of a vessel wall of the extracted vessel based on the generated 3-D tomographic image data, and detecting a coordinate of an inner surface of the vessel wall of the extracted vessel based on the generated 3-D motion contrast data.

Further features of the present disclosure will become apparent from the following description of exemplary embodiments with reference to the attached drawings.

DESCRIPTION OF THE EMBODIMENTS

Now, with reference to the accompanying drawings, an embodiment of the present disclosure is described in detail. In this embodiment, an SS-OCT apparatus is used to generate a tomographic image and a motion contrast image described later from a 3-D optical coherence tomographic signal obtained from a fundus. Then, an inner surface and an outer surface of a wall of a vessel (hereafter referred to as "vessel wall") in a retina are detected from the tomographic image and the motion contrast image that have been obtained, and a vessel wall thickness is further calculated.

Configurations described in the following embodiment are merely an example, and the present disclosure is not limited to the following embodiment. Not all combinations of features described in the following embodiment are necessarily essential to solutions of the present disclosure. In the embodiment, an object to be inspected is a human eye (fundus), but an object to which the present disclosure is applied is not limited thereto. For example, the OCT apparatus may be used for detecting a vessel in skin, an organ, or the like. Further, in the embodiment, an object to be imaged is the fundus of an eye, but another region, for example, an anterior segment of the eye may be the object to be imaged.

[Entire Configuration of Image Formation and Processing Device]

Figure 1:
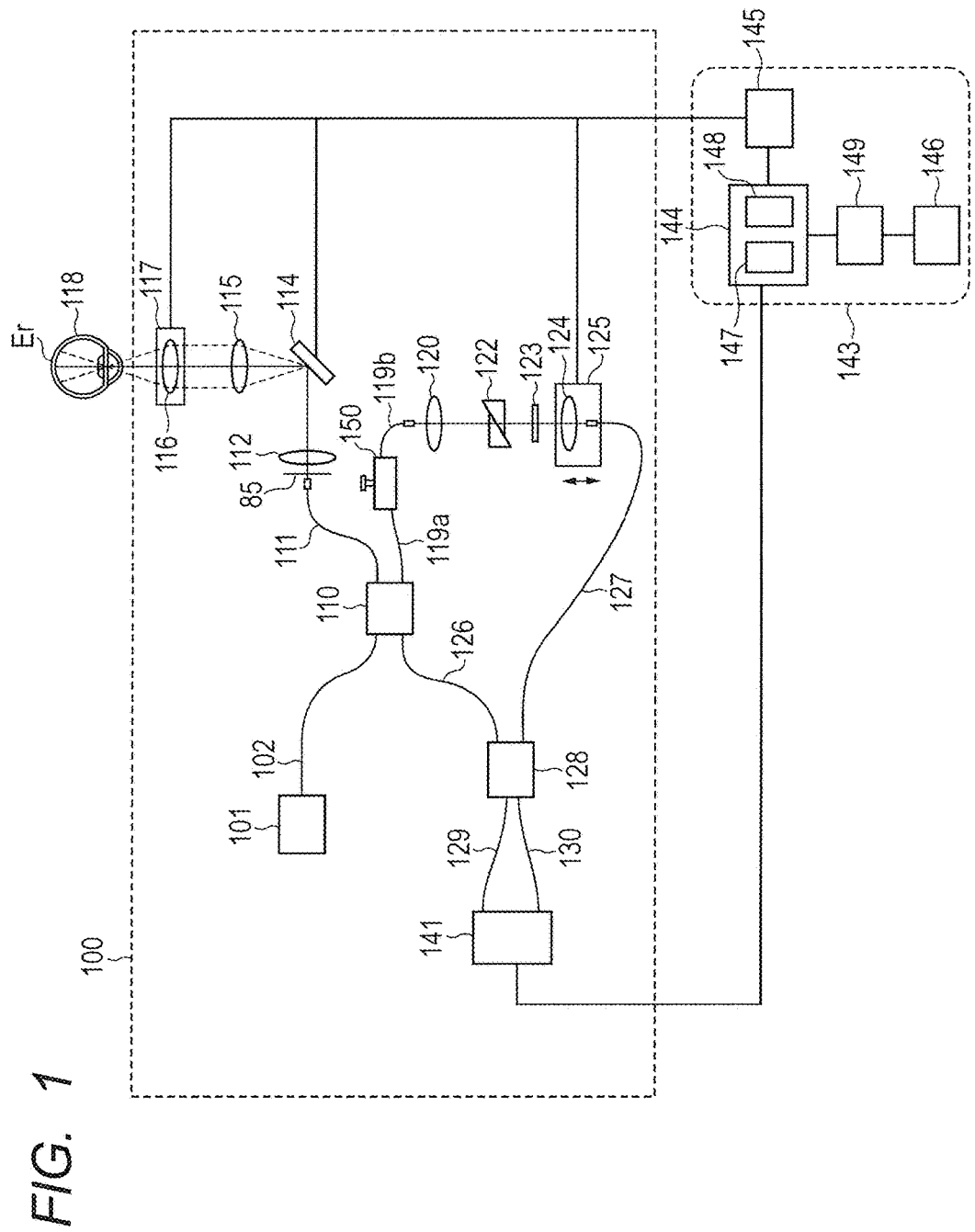
FIG. 1 is a schematic diagram for illustrating an example of an entire configuration of an OCT apparatus used in one embodiment of the present disclosure.

FIG. 1 is a diagram for illustrating a configuration example of an image formation and processing device according to one embodiment of the present disclosure, which includes an OCT apparatus configured to acquire a 3-D optical coherence tomographic signal and a control unit configured to control the OCT apparatus and to process an optical coherence tomographic signal. Specifically, in FIG. 1, an optical coherence tomographic signal acquiring unit 100 and a control unit 143 are illustrated.

<Configuration of Control Unit>

The control unit 143 includes a signal processing portion 144, a signal acquisition control portion 145, a display portion 146, and a display control portion 149. The signal processing portion 144 includes an image generating portion 147, and a map generating portion 148. In this case, the control unit 143 is, for example, a computer, and a CPU included in the computer is configured to execute a program stored in a storage device (not shown). This causes the computer to function as the signal processing portion 144, the signal acquisition control portion 145, the image generating portion 147, the map generating portion 148, and the display control portion 149.

The image generating portion 147 has a function of generating a luminance image and a motion contrast image from an electrical signal (interference signal) sent from a detector 141 of the optical coherence tomographic signal acquiring unit 100 described later. The map generating portion 148 has a function of generating layer information (segmentation of a retina) from the luminance image. The signal acquisition control portion 145 is configured to control the respective portions described above. The signal processing portion 144 is configured to perform various kinds of processing on the interference signal, to perform various kinds of processing on the generated image, to analyze the images, and to generate visible information on analysis results based on the interference signal output from the detector 141.

The images and the analysis results generated by the signal processing portion 144 are sent to the display control portion 149. The display control portion 149 is configured to display the images and the analysis results on a display screen of the display portion 146. In this case, a display formed of, for example, a liquid crystal display is used as the display portion 146. Image data generated by the signal processing portion 144 may be transmitted to the display portion 146 in a wired or wireless manner after being sent to the display control portion 149. Further, although the display portion 146 and other portions are included in the control unit 143 in this embodiment, the present disclosure is not limited thereto. The display portion 146 and other portions may be provided separately from the control unit 143, and may be, for example, a tablet computer, which is an example of a device that can be carried around by a user. In this case, it is preferred that the display portion 146 be provided with a touch panel function, and be configured to enable operations to be performed on the touch panel for movement of a display position of the image, magnification or reduction of the image, change of the image to be displayed, and the like.

Any numbers of CPUs and storage devices may be included in the control unit 143 as long as the numbers are at least one. That is, at least one processing device (CPU) and at least one storage device (at least one of a RAM and a ROM) are connected to the control unit 143. As a result, when at least one processing device executes the program stored in at least one storage device, the control unit 143 functions as the respective portions described above. The processing device is not limited to the CPU, and may be, for example, an FPGA.

<Configuration of Optical Coherence Tomographic Signal Acquiring Unit>

Next, a description is given of a configuration of the optical coherence tomographic signal acquiring unit 100. FIG. 1 is a diagram for illustrating a configuration example of an OCT apparatus used as the optical coherence tomographic signal acquiring unit in this embodiment. As the OCT apparatus, for example, an SD-OCT apparatus or an SS-OCT apparatus can be used. In this embodiment, the description is given of the configuration using the SS-OCT apparatus.

In the OCT apparatus, a swept-source (SS) light source is used as a light source 101. The light source 101 is configured to emit light while sweeping a wavelength of the light with a sweeping central wavelength of 1,050 nm and a sweeping width of 100 nm, for example. The values of the wavelength and the sweeping width are merely examples, and the present disclosure is not limited to those values. The same applies to the description of the following embodiment, that is, the described numerical values are merely examples, and the present disclosure is not limited to those numerical values.

The light emitted from the light source 101 is guided to a beam splitter 110 via an optical fiber 102 to be split into measuring light and reference light. The split ratio of the beam splitter 110 is 90 (reference light):10 (measuring light). The measuring light obtained through splitting is output to a measuring optical path via an optical fiber 111, and is converted into collimated light by a collimator 112. The measuring light converted into the collimated light enters an eye 118 to be inspected via a scan system 114, a scan lens 115, and a focus lens 116. A shutter 85 is arranged behind the collimator 112, and is inserted into the measuring optical path at a time of acquiring background data described later. The scan system 114 is configured to scan the measuring light onto a fundus Er of the eye 118. In this case, the scan system 114 is illustrated as a single mirror, but actually includes an X-axis scanner (not shown) and a Y-axis scanner (not shown) formed of galvano scanners so as to raster-scan the fundus Er of the eye 118 with the measuring light. As those scanners, not only the galvano scanners, but also, different kinds of known scanners, for example, a resonant scanner can be used.

The focus lens 116 is fixed on a stage 117, and is configured to move in an optical axis direction to adjust the focus of the measuring light. The scan system 114 and the stage 117 are controlled by the signal acquisition control portion 145 so that the measuring light can be scanned in a desired range of the fundus Er of the eye 118 (acquiring range of a tomographic image).

It is desired that the OCT apparatus be provided with a tracking function of detecting movement of the fundus Er to cause the mirrors of the scan system 114 to scan the light while following the movement of the fundus Er. A general technology can be used to perform a method for tracking, and the method for tracking may be performed in real time, or may be performed in post processing. As a method for tracking, there is given, for example, a method using a scanning laser ophthalmoscope (hereafter referred to as "SLO"). In this method, a 2-D image of the fundus Er (fundus surface image) within a plane perpendicular to an optical axis is acquired over time through use of SLO to extract a characteristic portion within the image, for example, a portion in which a vessel branches. How the characteristic portion within the acquired 2-D image has moved is then calculated as a moving amount of the fundus Er, and the calculated moving amount is fed back to the scan system 114. By the above-mentioned steps, real-time tracking can be performed for the movement of the fundus Er.

The measuring light is caused to enter the eye 118 by the focus lens 116 fixed on the stage 117 to be focused on the fundus Er. The measuring light irradiating the fundus Er is reflected or scattered at each layer of the retina, and travels on the above-mentioned measuring optical path backward as return light to return to the beam splitter 110. The return light entering the beam splitter 110 passes through an optical fiber 126 to enter a beam splitter 128. The beam splitter 128 and the beam splitter 110 described above may be a beam coupler.

The reference light obtained through splitting by the beam splitter 110 is output to the reference optical path via an optical fiber 119a, a polarization controller 150, and an optical fiber 119b, and is converted into collimated light by a collimator 120. The polarization controller 150 can change the polarization of the reference light into a desired polarization state. The reference light further passes through a dispersion compensation glass 122, an ND filter 123, and a collimator 124, to enter an optical fiber 127. The collimator 124 and one end of the optical fiber 127 are fixed on a coherence gate stage 125.

The coherence gate stage 125 is controlled by the signal acquisition control portion 145 so as to be driven in an optical axis direction depending on the difference in ocular axis length among subjects to be examined. Therefore, an optical path length of the reference light is changed as the coherence gate stage 125 is driven. Interference light described later is obtained under a condition that the optical path length of the reference light and an optical path length of the measuring light match each other. The optical path length of the reference light is changed in this embodiment, but the configuration for changing the optical path length is not limited thereto as long as an optical path length difference between the optical path of the measuring light and the optical path of the reference light can be changed.

The reference light passing through the optical fiber 127 enters the beam splitter 128. In the beam splitter 128, the return light of the measuring light and the reference light are combined to obtain interference light, and the interference light is further split into two beams. The split interference light beams are interference light beams having phases inverted to each other (hereafter expressed as a positive component and a negative component). The positive component of the split interference light passes through an optical fiber 129 to enter one input port of the detector 141. Meanwhile, the negative component of the interference light passes through an optical fiber 130 to enter another port of the detector 141. The detector 141 is a differential detector in which, when two interference light beams having phases inverted to each other by 180° are input, a DC component is removed, and the interference signal having only an interference component is output. The differential detector is used as a detector in this embodiment, but the mode of the detector is not limited thereto, and different kinds of known detectors can be used.

The interference light detected by the detector 141 is output as an electrical signal (interference signal) corresponding to the intensity of the light. The output interference signal is input to the signal processing portion 144, which is an example of a tomographic image generating portion.

[Scan Pattern]

In the OCT apparatus, measuring light scanning of radiating the measuring light to one point on the fundus of the eye 118 to acquire information relating to a cross section of the fundus at the one point in its depth direction is referred to as an A-scan. Further, measuring light scanning for acquiring information relating to a cross section of the eye 118 along a scanning plane in one direction, which is a direction orthogonal to the A-scan, that is, a 2-D image regarding a plane formed of the one direction and a depth direction is referred to as a B-scan. In addition, measuring light scanning in a direction orthogonal to both scanning directions for the A-scan and the B-scan (orthogonal to the plane of the 2-D image) is referred to as a C-scan.

In the OCT apparatus, when the measuring light is two-dimensionally raster-scanned on the fundus in order to acquire a three-dimensional tomographic image of the fundus, high-speed scanning is performed in the B-scan direction. Further, low-speed scanning is performed in the C-scan direction in order to scan the measuring light such that the scanning lines of the B-scan are aligned in a direction orthogonal to the B-scan direction. A two-dimensional tomographic image in the depth direction can be obtained by performing the A-scan and the B-scan, and a three-dimensional tomographic image can be obtained by performing the A-scan, the B-scan, and the C-scan. The measuring light is scanned in the B-scan and the C-scan by the above-mentioned scan system 114.

The X-axis scanner (not shown) and the Y-axis scanner (not shown) are formed of deflecting mirrors arranged so as to have their respective rotary axes orthogonal to each other. The X-axis scanner is configured to perform scanning in the X-axis direction through use of the measuring light, and the Y-axis scanner is configured to perform scanning in the Y-axis direction through use of the measuring light. The respective directions of the X-axis direction and the Y-axis direction are directions orthogonal to the direction of an ocular axis of an eyeball and orthogonal to each other. Such directions of line scanning as the B-scan direction and the C-scan direction may not necessarily match the X-axis direction and the Y-axis direction. Therefore, the directions for the line scanning of the B-scan and the C-scan can be determined appropriately depending on a 2-D tomographic image or a 3-D tomographic image to be acquired.

Next, an example of a scan pattern of the measuring light of this embodiment is described with reference to FIG. 2.

In OCTA, in order to measure the change with time of the OCT interference signal due to the blood flow, measurement is required to be performed a plurality of times at the same position (or substantially the same position). In this embodiment, the OCT apparatus performs scanning of repeating the B-scan at the same position m times, and then moving the scanning position of the measuring light to n y-positions. A specific scan pattern is illustrated in FIG. 2. At each of the n y-positions of y1 to yn on the fundus plane, the B-scan is repeated m times.

In order to correctly measure the change with time of the interference signal, those m times of B-scan are required to be performed at the same position on the fundus. However, the eye to be inspected always performs involuntary eye movement during fixation, and hence, the measuring light scanning at the same position is actually not easy, even when scanning is intended on the same scanning line. The measuring light scanning that is performed with the intention to B-scan the measuring light on the same-position scanning line is herein referred to as scanning the measuring light on the same scanning line, or acquiring the interference signal of the same cross section. Further, it is conceivable to execute the B-scan a plurality of times while slightly shifting the scanning line intentionally, and to perform averaging or other processing on the obtained interference signals regarding pixels corresponding thereto, to thereby reduce noise. In this case, those substantially equal scanning lines of the measuring light are expressed as the same scanning line, and further, the tomographic image obtained through the averaging or other processing is also expressed as the tomographic image obtained from the same scanning line.

In this case, as the value of m, which is the number of repetition times, becomes larger, the number of measurement times at the same position also increases, and an accuracy of detecting the blood flow increases. Meanwhile, the scan time increases, and hence, there arise fears that a motion artifact occurs in an image due to movement of an eye (involuntary eye movement during fixation) during a scan and that burden on the subject to be examined increases. In this embodiment, the number of repetition times m is determined as 4 in consideration of the balance between the detection accuracy and the measurement time. The control unit 143 may change m depending on an A-scan speed of the OCT apparatus, results of motion analysis of a fundus surface image of the eye 118, or the like.

Figure 2:
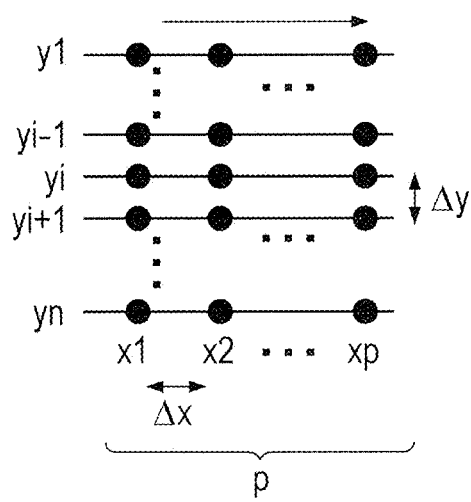
FIG. 2 is a diagram for illustrating a mode of scanning measuring light according to this embodiment.

In FIG. 2, p represents the number of samples of the A-scan in one B-scan. In other words, the size of the plane image is determined based on p×n. As p×n increases, a wider range can be scanned as long as a measurement pitch is the same. However, the scan time increases, and hence, the above-mentioned motion artifact and increase in the burden on the subject to be examined are required to be taken into consideration. In this embodiment, n=p=300 is set in consideration of a balance between the scan range and the scan time. The above-mentioned n and p can be freely changed as appropriate.

Further, $\Delta x$ of FIG. 2 is an interval (x-pitch) between x-positions that are adjacent A-scan positions, and $\Delta y$ of FIG. 2 is an interval (y-pitch) between y-positions that are adjacent B-scan positions. In this embodiment, the x-pitch and the y-pitch are determined as ½ of a beam spot diameter of the irradiation light on the fundus, and is set to 10 μm. The image to be generated can be formed with high definition by setting the x-pitch and the y-pitch to ½ of the beam spot diameter on the fundus. Even when the x-pitch and the y-pitch are set smaller than ½ of the beam spot diameter on the fundus, an effect of increasing the definition of the image to be generated to a level higher than that is small.

When the x-pitch and the y-pitch are set larger than ½ of the beam spot diameter on the fundus, the definition deteriorates, but a wide-range image can be acquired with a small data volume. Therefore, the x-pitch and the y-pitch may be changed freely depending on clinical demands. In this embodiment, the scan range is set to p×$\Delta x$=3 mm in an x direction and n×$\Delta y$=3 mm in a y direction in consideration of the above.

Figure 3:
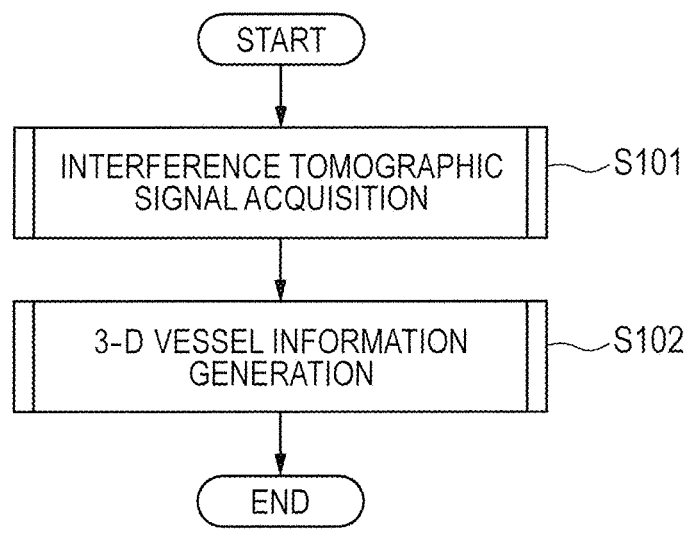
FIG. 3 is a flow chart for illustrating an example of an overall processing procedure according to this embodiment.

Next, with reference to a flow chart of FIG. 3, a description is given of a procedure of specific processing executed by the processing device according to this embodiment. In Step S101, the signal acquisition control portion 145 controls the optical coherence tomographic signal acquiring unit 100 to acquire an optical coherence tomographic signal. Details of the processing are described later. Next, in Step S102, the control unit 143 generates 3-D vessel information. Details of the processing are described later. In the processing device according to this embodiment, the above-mentioned steps are carried out to acquire or to display information relating to a wall thickness of a designated vessel on the fundus, and then processing of generating the 3-D vessel information is completed. The description of this embodiment is directed to a case when the interference signal obtained from the eye 118 is processed in real time to obtain information on the vessel wall. However, data relating to the eye 118, which is acquired and stored in a memory or the like in advance, may be read to perform the above-mentioned processing.

[Procedure for Acquiring Optical Coherence Tomographic Signal]

Figure 4:
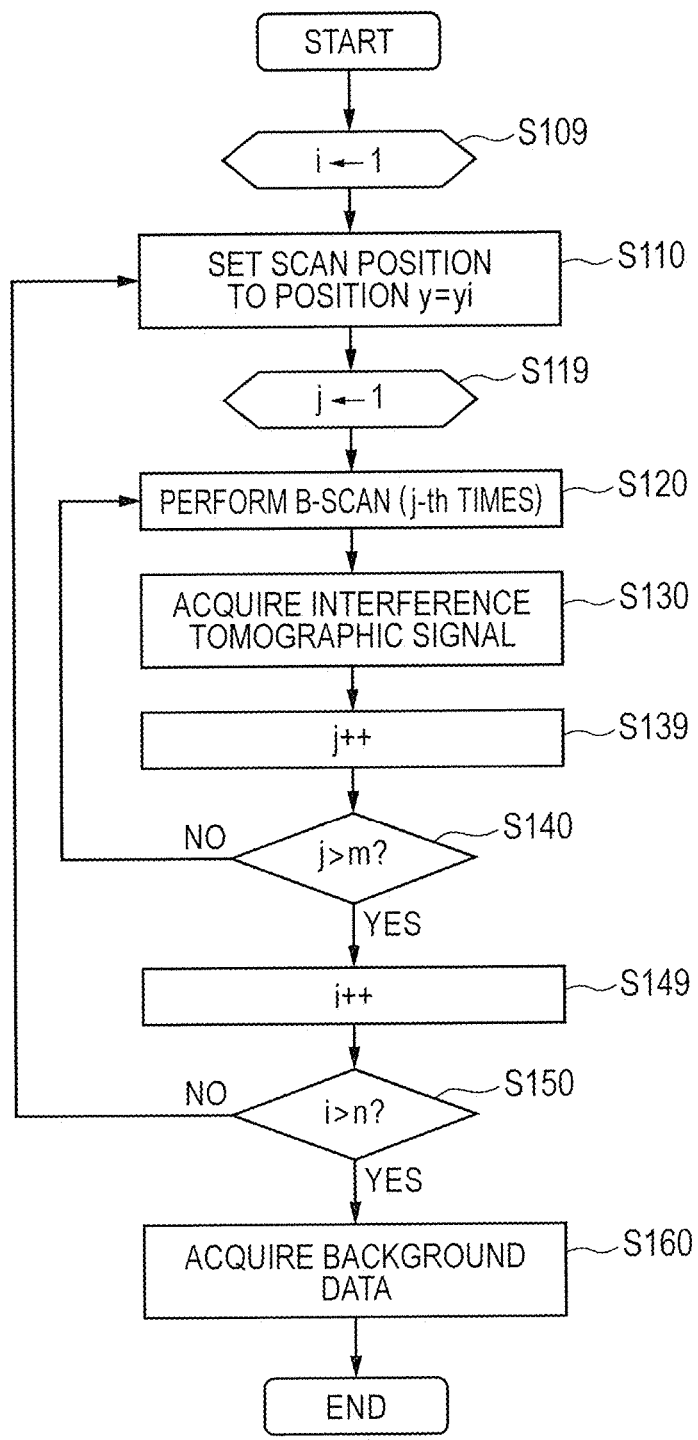
FIG. 4 is a flow chart for illustrating an example of a procedure for acquiring an interference signal according to this embodiment.

Next, with reference to a flow chart of FIG. 4, a description is given of a procedure of specific processing involving the acquisition of the optical coherence tomographic signal performed in Step S101 according to this embodiment. In this processing, first, in Step S109, the signal acquisition control portion 145 sets an index i of a position yi illustrated in FIG. 2 to 1. In Step S110, the optical coherence tomographic signal acquiring unit 100 moves the radiating position of the measuring light based on an instruction from the signal acquisition control portion 145 so that the position for executing the B-scan becomes yi. In Step S119, the signal acquisition control portion 145 sets an index j of the repeated B-scans to 1. In Step S120, OCT starts the repeated B-scans at the position yi.

In Step S130, the detector 141 detects the interference signal in each A-scan, and the interference signal is stored in the signal processing portion 144 via an A/D converter (not shown). The signal processing portion 144 acquires p samples of interference signals obtained in the A-scans, to thereby set the p samples of interference signals as an interference signal corresponding to one B-scan. When the first B-scan is completed at the position yi, in Step S139, the signal acquisition control portion 145 increments the index j of the repeated B-scans.

In Step S140, the signal acquisition control portion 145 determines whether or not j is larger than a predetermined number of times (m). That is, the signal acquisition control portion 145 determines whether or not the B-scan at the position yi has been repeated m times. When it is determined that the B-scan has not been repeated m times, the flow returns to Step S120 to repeat the B-scan on the scanning line at the same position, and the operation from Step S120 to Step S139 is repeated. When it is determined that the B-scan has been repeated m times being the predetermined number of times, the flow proceeds to Step S149.

In Step S149, the signal acquisition control portion 145 increments the index i of the position yi. In Step S150, the signal acquisition control portion 145 determines whether or not i is greater than a predetermined number of times n, that is, whether or not the B-scan has been carried out at all of the n y-positions. When it is determined that the predetermined number of times of measurement has not been reached, the flow returns to Step S110 to carry out a B-scan at the next y-position, and the subsequent steps from Step S119 to Step S149 are repeated. When the predetermined number of times of measurement at the y-position are completed (when yes), the flow proceeds to the next Step S160.

In Step S160, the optical coherence tomographic signal acquiring unit 100 acquires, for the interference signals obtained individually, background data corresponding to noise ascribable to an apparatus, or the like. Specifically, the optical coherence tomographic signal acquiring unit 100 acquires data based on 100 A-scans without obtaining the return light under a state in which the shutter 85 is inserted into the measuring optical path. The signal acquisition control portion 145 averages the data obtained in the 100 A-scans, and stores the data. The number of times of measuring a background is not limited to 100. After the acquisition of the background data, a procedure for acquiring the optical coherence tomographic signal is completed. In the same manner as the data relating to the eye 118, which is stored as described above, data stored in a memory, or the like, in advance may be read to be used as the optical coherence tomographic signal including the background data.

An interference signal set corresponding to one frame of the tomographic image is obtained from the one B-scan described above. The interference signal sets corresponding to a plurality of frames that form the same cross section are obtained from m times of B-scan described above. When m times of B-scan are to be performed to acquire motion contrast data described later in OCTA, the measurement requires a longer time as described above. In addition, the repetition is not performed in normal OCT, and hence, it is possible to acquire the data in a larger range in the same amount of time as in OCTA. Therefore, compared with a region for performing OCTA, a region for acquiring 3-D tomographic image data by the OCT apparatus is often set to a larger region including the region for OCTA. In this case, it is possible to reduce the measurement time by including the above-mentioned interference signal sets for OCTA corresponding to the plurality of frames in the interference signal sets of a plurality of frames for generating the 3-D tomographic image data to simultaneously acquire the interference signal sets. The above-mentioned acquisition of the interference signal sets is executed by the configuration functioning as a signal acquiring unit including the detector 141 and the signal acquisition control portion 145.

[Procedure for Processing of Generating 3-D Vessel Information]

Figure 5:
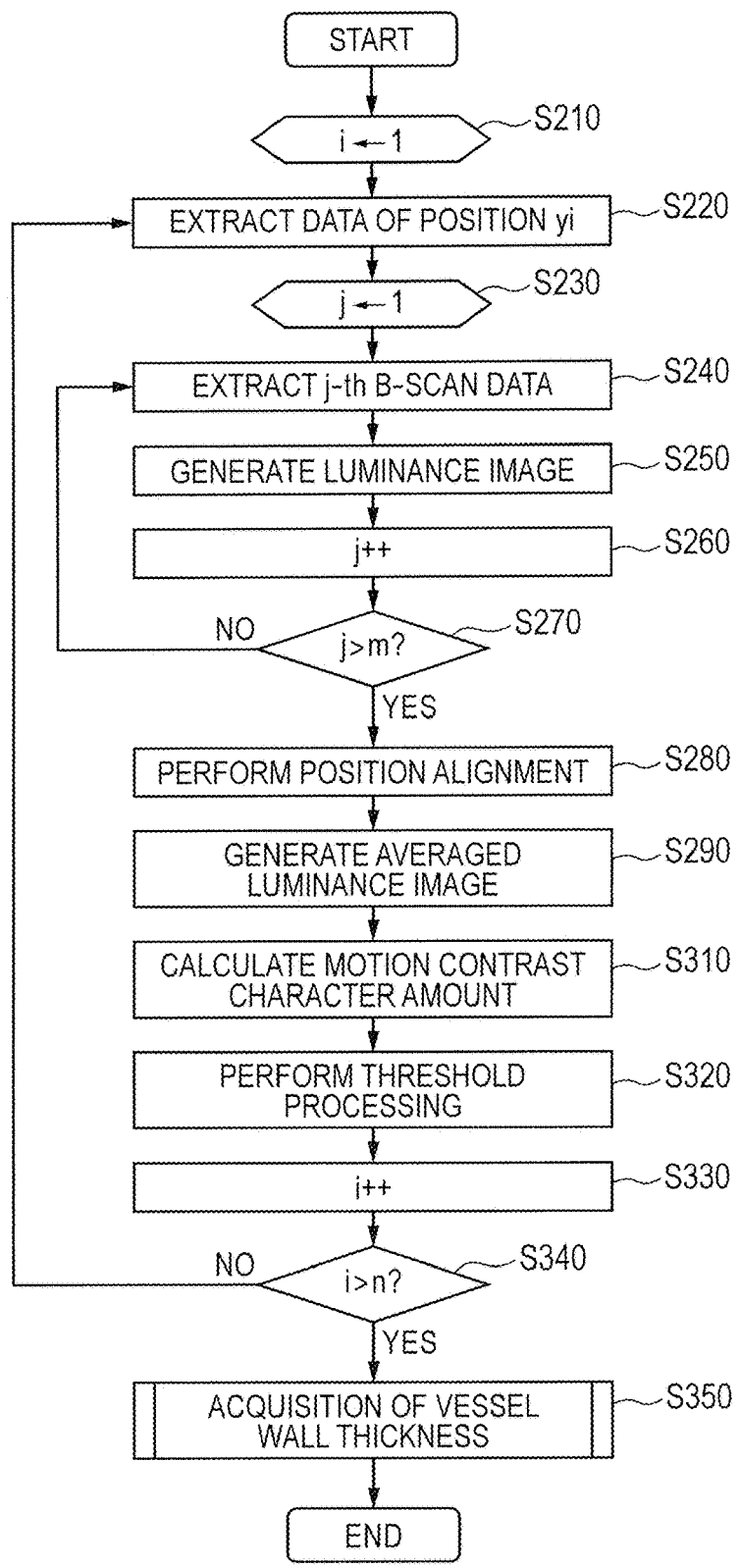
FIG. 5 is a flow chart for illustrating an example of a signal processing procedure for acquiring vessel information according to this embodiment.

Next, with reference to the flow chart of FIG. 5, a description is given of a procedure of specific processing involving the generation of the 3-D vessel information performed in Step S102 described above. In this embodiment, a motion contrast for OCTA needs to be calculated in order to generate the 3-D vessel information from OCTA information described later.

In this case, the motion contrast is defined as a contrast between a tissue involving flowing (for example, blood) and a tissue involving no flowing among tissues of the subject to be examined. Specifically, an image indicating a character amount, for example, a degree of dispersion of pixels of a portion with time modulation among a plurality of tomographic images of the same cross section, is referred to as a motion contrast image. Further, a pixel value for the motion contrast image is defined as a motion contrast. The motion contrast, a method of acquiring the motion contrast, and the like, which are referred to in this embodiment, are described later.

In this processing, first in Step S210, the signal processing portion 144 sets the index i of the position yi to 1. In Step S220, the signal processing portion 144 extracts the interference signals corresponding to m times (B-scan data), which have been obtained by the repeated B-scans at the position yi, from the data stored in a storage portion, for example, a memory (not shown). In Step S230, the signal processing portion 144 sets the index j of the repeated B-scans to 1. In Step S240, the signal processing portion 144 extracts the j-th B-scan data.

In Step S250, the signal processing portion 144 performs general reconstruction processing on the B-scan data extracted in Step S240, to thereby generate a luminance image of the tomographic image. In the generation of the luminance image, the image generating portion 147 first removes fixed pattern noise formed of the background data from the interference signal. The fixed pattern noise is removed by averaging the A-scan signals of a plurality of pieces of detected background data to extract the fixed pattern noise and subtracting the fixed pattern noise from the input interference signal. Next, the image generating portion 147 performs desired window function processing in order to optimize the depth resolution and the dynamic range that have a trade-off relationship when Fourier transform is performed at a finite interval. After that, the image generating portion 147 performs FFT processing to generate the luminance image of the tomographic image.

After the luminance image generation, in Step S260, the signal processing portion 144 increments the index j of the data on the repeated B-scans to be extracted. In Step S270, the signal processing portion 144 determines whether or not the number of extracted pieces of B-scan data is greater than m. That is, the signal processing portion 144 determines whether or not the generation of the luminance image based on the B-scan data at the position yi has been repeated m times. When the generation of the luminance image has not reached m times, the flow returns to Step S240 to repeat the generation of the luminance image based on the B-scan data obtained by the repeated B-scans at the same position yi. That is, the image generating portion 147 repeats the processing from Step S240 to Step S260 to acquire a plurality of luminance images (tomographic images) at substantially the same location of the eye 118.

When it is determined in Step S270 that the generation of the luminance image has reached m times, the flow proceeds to Step S280. In Step S280, the signal processing portion 144 performs position alignment of the m frames of the luminance image at the same position yi obtained in the above-mentioned steps from Step S240 to Step S260. Specifically, the signal processing portion 144 first selects one arbitrary frame from the m frames as a luminance image for a template. The frame to be selected as a template may be selected by calculating correlations in all of the combinations, obtaining the sum of correlation coefficients for each frame, and selecting the frame having the maximum sum.

Next, the signal processing portion 144 obtains misalignment amounts ($\delta X$, $\delta Y$, and $\delta \theta$) by comparing the template with each frame. Specifically, the signal processing portion 144 calculates a normalized cross-correlation (NCC) that is an index representing a similarity with the image of the frame to be compared with while changing the position and the angle of the template image, and obtains as the misalignment amounts a difference of an image position exhibited when the value of NCC is the maximum. The signal processing portion 144 further applies position correction to the (m−1) frames other than the template in accordance with the misalignment amounts ($\delta X$, $\delta Y$, and $\delta \theta$), to thereby perform the position alignment of the m frames.

Various changes can be made to the index representing the similarity, as long as the index is a scale representing the similarity between characteristics of the images in the template and the frame. For example, a sum of absolute difference (SAD), a sum of squared difference (SSD), or a zero-means normalized cross-correlation (ZNCC) may be used. Further, a phase only correlation (POC) or a rotation invariant phase only correlation (RIPOC) may be used.

After the position alignment of the m frames is completed, in Step S290, the signal processing portion 144 averages the luminance images subjected to the position alignment in Step S280 to generate an averaged luminance image. The averaged luminance image is used at a time of threshold processing described later. As the mode of the averaging, the averaging may be executed by combining at least two interference signal sets corresponding to a plurality of frames in a superimposed manner.

After the averaged luminance image is generated, in Step S310, the image generating portion 147 executes the calculation of the motion contrast. In this embodiment, a dispersion value of a signal intensity (luminance) is calculated for each pixel at the same position from the m frames of the luminance image subjected to the position alignment by the signal processing portion 144 in Step S280, and this dispersion value is set as the motion contrast. That is, the image generating portion 147 calculates the motion contrast through use of pixel data on the corresponding pixels among the respective plurality of luminance images at the same position. Other than the dispersion value, any one of a standard deviation, a difference value, a decorrelation value, and a correlation value may be used. That is, any index representing a change in luminance value among the respective pixels of a plurality of B-scan images at the same y-position can be used as the motion contrast. Further, the phase may be used instead of the signal intensity.

The motion contrast can also use a variation coefficient that is normalized by an average value of each pixel at the same position in each frame, instead of the dispersion value of each pixel at the same position in the luminance images of the m frames of tomographic images. In this case, the motion contrast is independent of the pixel values indicating the structure of a retina, and it is possible to obtain a motion contrast having higher sensitivity.

In Step S320, the signal processing portion 144 performs threshold processing on the calculated motion contrast. In this embodiment, the signal processing portion 144 extracts an area in which only random noise is displayed from the averaged luminance image calculated in Step S310, and calculates a standard deviation $\sigma$ for the area to set "(averaged luminance of noise floor)+$2\sigma$" as a threshold value. The signal processing portion 144 sets the value of the motion contrast of a pixel having a luminance value equal to or less than the threshold value to 0 to disable the pixel data. By the threshold processing of Step S320, it is possible to remove the motion contrast derived from a change in luminance due to the random noise, and to reduce noise.

As the threshold value becomes less, a detection sensitivity for the motion contrast increases, and noise components also increase. In contrast, as the threshold value becomes greater, the noise components decrease, but the detection sensitivity for the motion contrast is lowered. In view of the above-mentioned fact, the threshold value is set to "(averaged luminance of noise floor)+$2\sigma$" in this embodiment, but the threshold value is not limited thereto.

After the threshold processing is completed, in Step S330, the signal processing portion 144 increments the index i of the position yi. In Step S340, the signal processing portion 144 determines whether or not i is greater than n. That is, the signal processing portion 144 determines whether or not the position alignment, the generation of the averaged luminance image, the calculation of the motion contrast, and the threshold processing have been completed at all of the n y-positions. When there is a y-position at which the processing has not been completed, the flow returns to Step S220. After that, those pieces of processing are repeated until the processing from Step S220 to Step S330 has been completed at all of the y-positions. When all the pieces of processing have been completed, the flow proceeds to the next Step S350.

In Step S340, it is determined whether or not i has become greater than n and the above-mentioned processing has been completed at all of the y-positions. When the processing has been completed, the averaged luminance images have been generated and the motion contrasts have been acquired for the B-scan images (luminance images in a retinal cross section along the B-scan line) at all of the y-positions. The B-scan images at a plurality of y-positions correspond to the 3-D tomographic image data in a scan area of the measuring light, and the motion contrast data obtained at those y-positions also corresponds to data in three dimensions. As described above, the signal processing portion 144 functions as a 3-D tomographic data generating unit configured to generate the 3-D tomographic image data and a 3-D motion contrast generating unit configured to generate 3-D motion contrast data.

Figure 6:
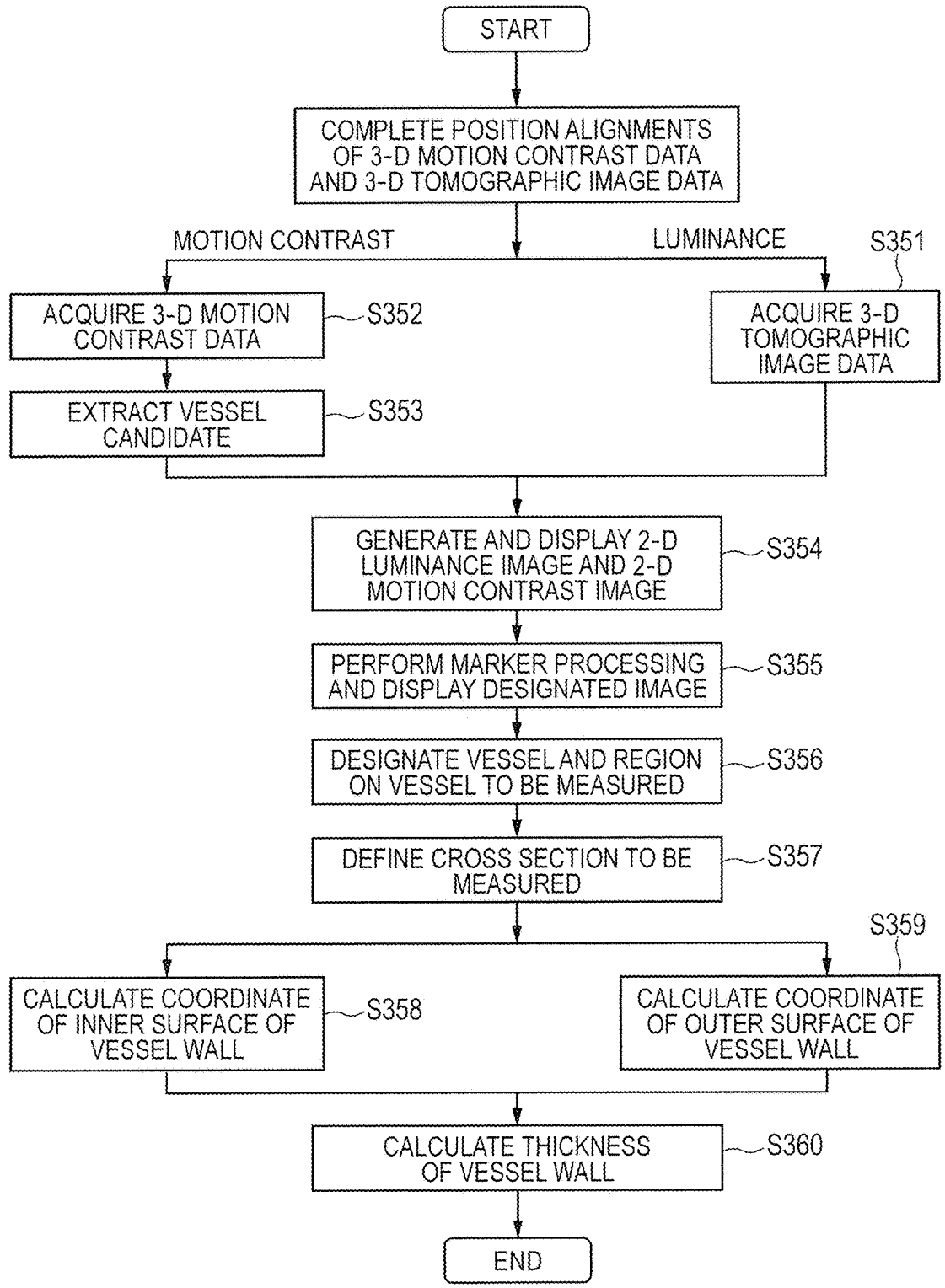
FIG. 6 is a flow chart for illustrating an example of a procedure for acquiring a vessel wall thickness according to this embodiment.

In Step S350, the signal processing portion 144 performs processing for acquiring a vessel wall thickness through use of 3-D data on the motion contrast. After the vessel wall thickness is acquired, it is determined that the 3-D vessel information has been generated, and the processing illustrated in the flowchart is completed. Next, with reference to FIG. 6, the processing for acquiring the vessel wall thickness to be executed in Step S350 is described in detail. FIG. 6 is a flow chart for illustrating processing for calculating the vessel wall thickness based on the acquired data on the 3-D motion contrast and the luminance. As described above, in this embodiment, the 3-D tomographic image data and the 3-D motion contrast data are pieces of data subjected to the position alignment between the pixels corresponding to each other. The subsequent processing presupposes that the above-mentioned position alignment of data has been completed.

[Procedure of Processing for Calculating Vessel Wall Thickness]

In Step S351, the signal processing portion 144 acquires the previously obtained 3-D tomographic image data (luminance image). In Step S352, the signal processing portion 144 acquires the 3-D motion contrast data. In this embodiment, the 3-D tomographic image data and the 3-D motion contrast data are obtained from the same B-scan data. Therefore, the scan area, the respective pixels in a 3-D space within the scan area, the spatial resolution (sample pitch), the depth resolution, and the like, are the same between both the pieces of data. Therefore, the position alignment between both the pieces of data is considered to have already been completed, and superimposition processing described later, or the like, can be executed as it is in a manner of the flow chart illustrated in FIG. 6.

However, the 3-D tomographic image data and the 3-D motion contrast data may be obtained from B-scans that are different from each other. For example, when the 3-D tomographic image data is acquired, a scan range of the B-scan relating to the same cross section is set greater than a scan range of the B-scan performed to acquire the 3-D motion contrast data, and the acquisition may be executed as each individual scan. Further, it is preferred that the processing for averaging be performed when the 3-D tomographic image data is acquired, but in this case, the 3-D tomographic image data may be obtained by one B-scan and one C-scan. Also, in this case, the 3-D tomographic image data and the 3-D motion contrast data may be normalized so as to have an equal resolution, and the position alignment may be further performed. By such pre-processing, the subsequent processing within the flow chart illustrated in FIG. 6 can be performed in the same manner.

(Vessel Candidate Extracting Processing)

The signal processing portion 144 can extract a vessel candidate from the 3-D tomographic image data or the 3-D motion contrast data. To extract the vessel candidate, luminance information on the 3-D tomographic image data may be used, or the motion contrast information may be used. In this embodiment, as illustrated in FIG. 6, in Step S353, the signal processing portion 144 extracts the vessel candidate through use of the 3-D motion contrast data. At that time, the signal processing portion 144 performs the threshold processing on the data on the respective pixels, and recognizes, as a pixel of the vessel candidate, a pixel indicating data having the 3-D motion contrast data equal to or greater than a predetermined threshold value. Also, when the 3-D tomographic image data is used, the signal processing portion 144 performs the threshold processing on the data on the respective pixels, and recognizes the pixel of the vessel candidate.

The pieces of data evaluated as the vessel candidate at this time may include data derived from random noise and data on a minute vessel that does not correspond to an object to be measured. In order to effectively avoid those pieces of data, it is desired to take the connective relationship between vessels into consideration. Hence, the number of successive pixels in terms of the motion contrast data among the respective vessel candidates is evaluated to estimate the connectivity of the vessel from the length in number of pixels. That is, it is possible to automatically extract a vessel candidate useful as an object to be measured by separately designating a threshold value relating to the number of successive pixels in a case where pixels exceeding a predetermined threshold value are successively arranged, and recognizing that a pixel group, which is included in the successive pixels evaluated as a vessel candidate and has a connection including a predetermined number or more of pixels, indicates a vessel. That is, a vessel extracting unit recognizes, as a vessel, the above-mentioned pixel group being the pixels of the vessel candidate and including a predetermined number or more of successive pixels.

(Generation and Display of 2-D Image)

After the vessel candidate is extracted, in Step S354, the map generating portion 148 performs segmentation processing. Specifically, the map generating portion 148 identifies each layer in the retina by performing comparison processing between a luminance profile of the 3-D tomographic image data in the depth direction and a threshold value corresponding to each layer or a layer boundary. After the identification, the values of respective pixels within a specific layer interval or within a predetermined range in the depth direction are projected or integrated in the depth direction to generate 2-D image data. In addition, a 2-D image referred to as an enface luminance image is generated based on the 2-D image data. In this embodiment, the respective pixels for presenting the 3-D motion contrast data correspond to the respective pixels for presenting the 3-D tomographic image data. Therefore, the same processing is also performed for the 3-D motion contrast data to generate 2-D motion contrast data. At that time, data on pixels, the number of which is equal to or smaller than the above-mentioned predetermined threshold value, is disabled because of being determined as pixels corresponding to a tissue that does not include a vessel, and the value of the motion contrast is set to, for example, 0. It is possible to more clearly present information relating to blood flow in a 3-D space by generating the 2-D motion contrast data including the pixel of the disabled data. At the same time, a 2-D motion contrast enface image corresponding to the enface luminance image is generated based on the 2-D motion contrast data.

In OCTA, a constituent existing in the blood flow, namely, a lumen of the vessel is extracted. The retinal vessel wall is substantially transparent, and hence a subject to be extracted in another angiography is the same. Meanwhile, the luminance image obtained by the OCT apparatus is obtained by detecting reflection or scattering due to the outer surface of the vessel wall as the interference light. Hence, the inner surface structure of the vessel wall in contact with blood can be extracted from the motion contrast image, and the outer surface structure of the vessel wall can be extracted from the luminance image. Therefore, the vessel matched in both the images is set as a vessel to be measured being the object to be measured, and a difference between the two images regarding the vessel is obtained, to thereby be able to acquire information on a vessel wall thickness useful for diagnosis.

Figure 8:
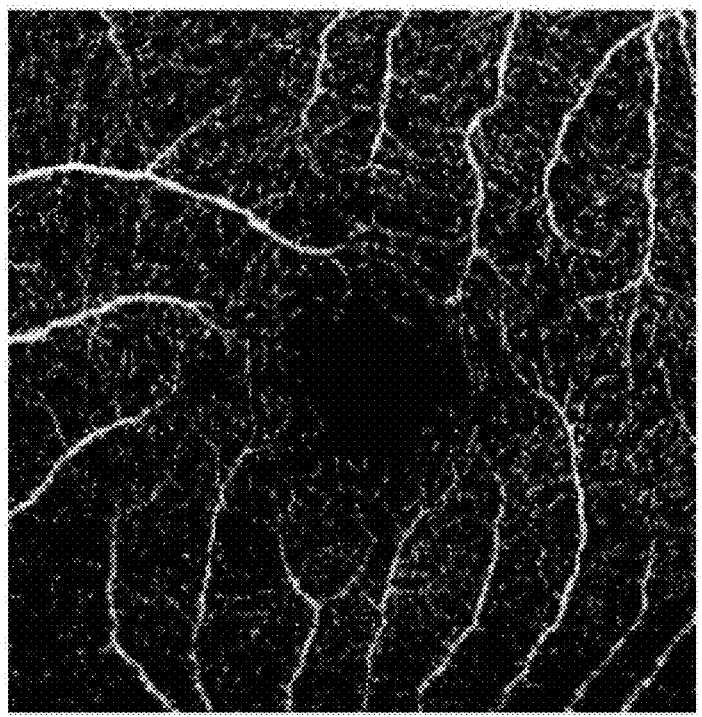
FIG. 8 is a diagram for illustrating an example of a motion contrast image according to this embodiment.

The generated 2-D motion contrast enface image exemplified in FIG. 8 is displayed on the display portion 146 by the display control portion 149. When the vessel candidate can be extracted and recognized from the image, a 2-D enface luminance image may be displayed on the display portion 146. In this embodiment, in order to generate the enface luminance image or the 2-D motion contrast enface image, the corresponding pixel values are integrated. However, the enface luminance image can also be generated by extracting representative values, for example, maximum values, minimum values, and median values of the respective pixel values and projecting or integrating the representative values. In this embodiment, only the 2-D motion contrast enface image is displayed, but both the 2-D motion contrast enface image and the enface luminance image may be displayed in different colors in a superimposed manner as the need arises.

(Marker Processing and Display of Designation Image)

Figure 9:
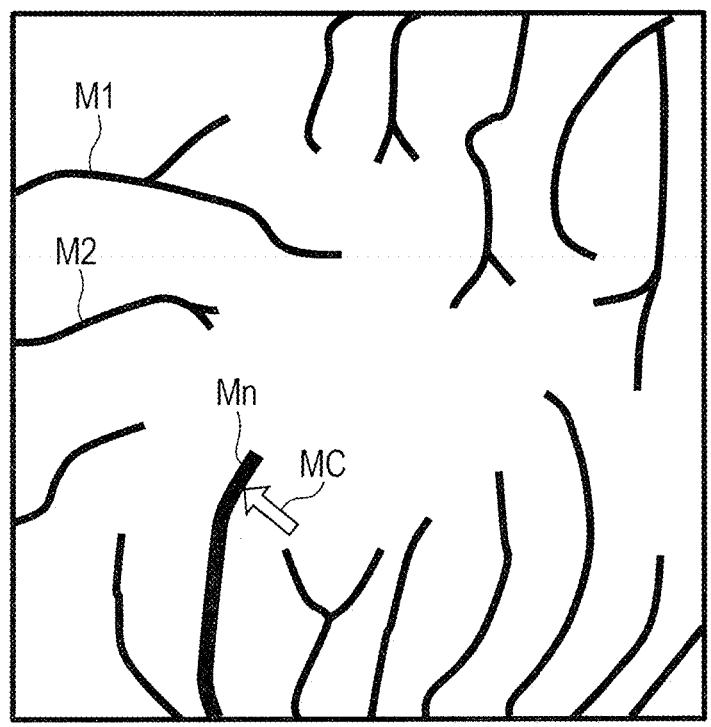
FIG. 9 is a diagram for illustrating an example of a display mode of a vessel candidate on a GUI according to this embodiment.

After the 2-D image is displayed, in Step S355, the signal processing portion 144 instructs the display control portion 149 to highlight the extracted vessel candidate on the display screen by adding a marker. The highlight using the marker allows the user to be notified of the location of the extracted vessel. Specifically, the 2-D motion contrast enface image is displayed on the display portion 146, and the marker indicating the vessel candidate is further displayed at a pixel coordinate corresponding to the vessel candidate extracted from the 3-D motion contrast data in a superimposed manner so as to enable each vessel candidate to be identified. FIG. 9 is an example of display on the display portion 146, and the image of FIG. 9 serves as a designation image for designating a vessel having a wall thickness to be measured and a region on the vessel. In the display example, M1, M2, . . . , and Mn are the markers of all the extracted vessels. On the display screen, a mouse cursor MC is displayed in a superimposed manner. In this embodiment, the display portion 146 corresponds to a display unit configured to display at least one of the 2-D image and the 2-D motion contrast image (enface luminance image and 2-D motion contrast enface image). The display control portion 149 corresponds to a unit configured to display the above-mentioned display mode for designating a region to be measured on the display portion 146, to receive a designation command input to the display mode, and to input the designation to the signal processing portion 144.

(Designation of Vessel to be Measured and Region to be Measured)

Figure 7:
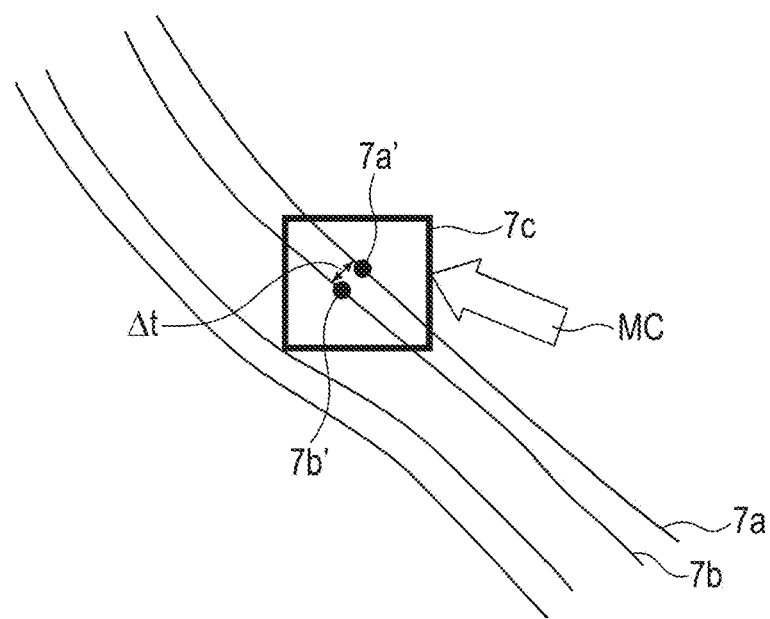
FIG. 7 is an explanatory diagram for illustrating an example of a method of calculating the vessel wall thickness according to this embodiment.

In Step S356, the user recognizes the displayed marker as the extracted vessel, and designates a region on the marker where the vessel wall thickness is to be measured by clicking on the region with a pointing device, for example, a mouse. An exemplary UI thereof is described below. First, when the user moves the mouse cursor MC closer to the marker corresponding to a desired vessel candidate, only that marker is highlighted, and even overlapping vessels, for example, can be distinguished from each other. In this case, the user moves the mouse cursor MC to a position approximately close to the region on the highlighted marker where the wall thickness is to be measured. When a click is performed with the mouse in this state, a frame 7c as illustrated in, for example, FIG. 7, is displayed. At the same time, markers at two points of an outer surface coordinate and an inner surface coordinate are displayed as points of measurement of the vessel wall thickness. When the user further performs a click with the mouse under this state, the selection of the region to be measured is determined.

As described later, the measurement of the vessel wall thickness at the designated position is executed in the following flow. However, when both the 2-D motion contrast enface image and the enface luminance image are superimposed on each other and a desired vessel region is further magnified, it is possible to intuitively recognize the structure of the inner surface and the outer surface of the vessel wall without measuring the image. For example, the vicinity of the region where the vessel wall thickness is to be measured may be highly magnified as illustrated in FIG. 7 and may be displayed once a click is performed with the mouse after the mouse cursor MC is put in the vicinity of the region to be measured. The superimposition of images (superimposition processing) and the magnification processing can facilitate the grasp of an inner surface 7b of the vessel wall (motion contrast enface image) and an outer surface 7a of the vessel wall (enface luminance image) within the 2-D image. In this case, when two points corresponding to an inner surface point 7b' and an outer surface point 7a' of the vessel in the region to be measured, which are visually recognized on the 2-D image, are designated and a distance between the two points is measured, the vessel wall thickness at the position can also be uniquely obtained. It is also possible to easily obtain the wall thickness with more accuracy by designating four points along a cutting-plane line substantially orthogonal to the vessel wall as a cross section of the vessel, and measuring a distance between points that form a pair.

(Calculation of Measured Cross Section)

However, in an actual case, the distance between two individually designated points does not easily match the vessel wall thickness in the region with accuracy. In order to correctly obtain the vessel wall thickness, it is necessary to define a cross section orthogonal to a vessel travel direction in the vicinity of the above-mentioned region to be measured. In this embodiment, in Step S357, a result of estimating the above-mentioned connectivity of the vessel is used. That is, when there are at least two pixels, desirably at least three pixels, of connective data, an average connective direction of those pixels is handled as a vector to obtain a direction vector from a difference in X, Y, and Z coordinates. This direction vector is defined as the vessel travel direction. In addition, when a consideration is given to a plane orthogonal to the vessel travel direction at one pixel coordinate in a vessel connective portion, this plane can be defined as the cross-section of the vessel.

Figure 10:
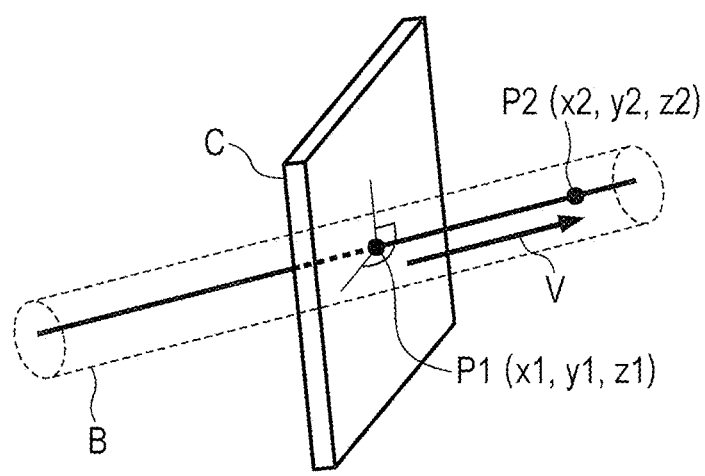
FIG. 10 is a diagram for illustrating a method of acquiring information on a vessel travel direction according to this embodiment.

FIG. 10 is a diagram for illustrating a method of determining a measured cross section. In FIG. 10, the vessel to be measured is represented by B, a target pixel on the vessel B is represented by P1, and a pixel connected to P1 is represented by P2. The respective pixel coordinates of P1 and P2 are set as (x1,y1,z1) and (x2,y2,z2). In this case, a vector V indicating the vessel travel direction is defined as (x2−x1,y2−y1,z2−z1). When the plane having the vector V as a normal is represented by C, an orthogonal plane being the measured cross section can be uniquely defined. The cross section is superimposed as the cutting-plane line on the magnified image illustrated in FIG. 7, and a distance between intersection points between the cutting-plane line and the outer surface 7a of the vessel wall and between the cutting-plane line and an inner surface 7b of the vessel wall is measured, to thereby allow the vessel wall thickness in this region to be known with accuracy.

(Calculation of Outer Surface Coordinate and Inner Surface Coordinate)

In Step S358, the signal processing portion 144 calculates the coordinate of an inner surface of the vessel wall.

Regarding the calculation, the motion contrast data corresponding to the vessel cross section is generated from the 3-D motion contrast data, and the generated data is used to calculate the inner surface coordinate, to thereby allow a thickness of the vessel wall to be measured with a geometrically correct positional relationship. In the same manner, regarding the calculation of the coordinate of the outer surface of the vessel wall in Step S359, the tomographic image data corresponding to the same vessel cross section may be generated from the 3-D tomographic image data, and the generated data may be used to calculate the outer surface coordinate.

Next, a specific description is given of processing for calculating the inner surface coordinate which is executed in Step S358. In Step S358, the inner surface structure of the same vessel wall as that of the vessel to be measured, which is previously extracted, is extracted from the 3-D motion contrast data acquired in Step S352. The inner surface of the vessel wall matches an outer periphery of blood (blood column) flowing through a vessel cavity. Hence, the inner surface structure of the same vessel wall of the vessel to be measured is obtained from the motion contrast data, and the inner surface coordinate on the measured cross section is detected from the positional information on the edge. In this processing, the signal processing portion 144 functions as an inner surface coordinate detecting unit configured to detect the coordinate of the inner surface of the vessel wall corresponding to the region designated on the vessel to be measured.

Next, a specific description is given of processing for calculating the outer surface coordinate executed in Step S359. In Step S359, the outer surface structure of the vessel wall of the vessel to be measured is extracted from the 3-D tomographic image data acquired in Step S351. The vessel wall is substantially transparent, but the luminance image acquired by the OCT apparatus is based on an intensity of reflected light generated from a difference in refractive index of the retinal structure, and hence, information on the outer surface of the vessel can be acquired satisfactorily. Then, the coordinate of the outer surface of the vessel wall on the measured cross section is detected from the positional information on the edge of the outer surface of the vessel wall. In this processing, the signal processing portion 144 functions as an outer surface coordinate detecting unit configured to detect the coordinate of the outer surface of the vessel wall corresponding to the region designated on the vessel to be measured.

When the motion contrast image is generated, each luminance is set so that a pixel value for a motion contrast equal to or smaller than a given threshold value is zero. Therefore, the given threshold value needs to be set appropriately in order to correctly detect the coordinate of the inner surface of the vessel wall. In this embodiment, in order to remove the motion contrast derived from the random noise, the threshold value is set to "(averaged luminance)+2σ" based on the averaged luminance of the noise floor and the standard deviation σ of all the images. However, the threshold value may be adjustable, or may be determined based on luminance information on a region (attention area) around the vessel to be measured.

(Calculation of Vessel Wall Thickness)

After calculating the inner surface coordinate and the outer surface coordinate, in Step S360, the signal processing portion 144 calculates the vessel wall thickness from the inner surface coordinate obtained in Step S358 and the outer surface coordinate obtained in Step S359. As described above with reference to FIG. 7, the outer surface 7a of the vessel wall and the inner surface 7b of the vessel wall represent the edges of the outer surface structure and the inner surface structure, respectively, of the vessel wall of the vessel to be measured, and the respective points of measurement corresponding to the same region are represented by the outer surface point 7a' and the inner surface point 7b'. A distance between the two points is equal to the thickness of the vessel wall, and hence the vessel wall thickness Δt is obtained by calculating the distance. After the vessel wall thickness is calculated, the processing for calculating the vessel wall thickness is completed. A result of the calculation is displayed on the display screen illustrated in FIG. 7.

As described above, this embodiment provides an OCT data processing method for executing the above-mentioned various kinds of processing for OCT data obtained by the OCT apparatus to obtain information relating to the vessel wall regarding the designated region on the vessel to be measured, more specifically, the inner surface coordinate and the outer surface coordinate. In this embodiment, the designation of the region to be measured is performed via the display screen. However, in the processing for obtaining the measured cross section, a wall thickness of the vessel on an automatically determined measured cross section may be calculated, a ratio of a vessel diameter and the wall thickness on the measured cross section may be compared with a predetermined value, and the region to be measured may be automatically designated based on a result of the comparison. Further, through display of the 2-D motion contrast enface image and the enface luminance image in a superimposed manner, it is possible to easily grasp the thickness of the vessel wall of each vessel simply as a distance between display parts of the two images along a direction orthogonal to the vessel wall. The region to be measured may be automatically designated from a ratio of the above-mentioned distance and a distance between the edges of the image corresponding to the vessel on the 2-D motion contrast enface image or the enface luminance image along the orthogonal direction. When receiving an instruction for the designation performed automatically, the signal processing portion 144 executes the above-mentioned processing for calculating the vessel wall thickness.

(3-D Data Processing)

In the description given above, the vessel wall thickness is measured as the distance between the two points 7a' and 7b' on the superimposition image of the 2-D motion contrast enface image and the enface luminance image, which is exemplified in FIG. 7. However, the vessel is actually tubular tissue, and it is conceivable that a state of the vessel cannot be accurately grasped from the displayed image. Therefore, it is desired to grasp the wall thickness for the entire perimeter of the vessel in the designated region. For example, in a case of a model displayed in FIG. 10, the coordinate of P1 within a plane C is estimated as a center position of the vessel. The 3-D motion contrast data and the 3-D tomographic image data have already been acquired. Through reconstruction of those pieces of data within the plane C, it is also possible to generate, for example, a tubular vessel cross section image. Therefore, a difference in distance between the inner surface of the vessel wall and the outer surface of the vessel wall is obtained from the coordinate of P1, to thereby obtain dimensional information relating to the vessel wall in the designated region.

In this case, it is preferred that the 3-D image of the vessel obtained through the superimposition of the 3-D motion contrast data and the 3-D tomographic image data be displayed as a screen for displaying the results. More specifically, the designated vessel, the designated region on the designated vessel, and its vicinity may be highly magnified to be three-dimensionally displayed as a vessel cross-sectional view, and the numerical values of the average thickness, minimum thickness, maximum thickness, standard deviation, and the like of the vessel wall in the designated region may be further displayed in a superimposed manner. In the case of this embodiment, the 3-D motion contrast data and the 3-D tomographic image data have already been acquired in advance, and hence the displayed results can also be changed as the region to be measured is moved on a designation screen for the region to be measured.

(Measurement of Plurality of Successive Cross Sections)

In actual diagnosis of a vessel, it is important to evaluate continuity of the travel of the vessel. In the above-mentioned embodiment, one orthogonal plane is set as the cross section for obtaining the vessel wall thickness. However, at least three proximal orthogonal planes corresponding to the connected pixels may be defined to generate the tomographic image data and the motion contrast data that correspond to those planes. In this case, through the same processing as the above-mentioned processing for each of the planes, it is possible to detect a plurality of successive outer surface coordinates and successive inner surface coordinates. In addition, successive vessel wall thicknesses can be calculated from distances between the outer surface coordinates and the inner surface coordinates being results of the detection. It is also possible to designate a start point and an end point of the measurement on the vessel, to define orthogonal planes proximal to each other at an interval defined in advance, and to calculate the vessel wall thicknesses on the designated sections.

(Trend Prediction)

Figure 11:
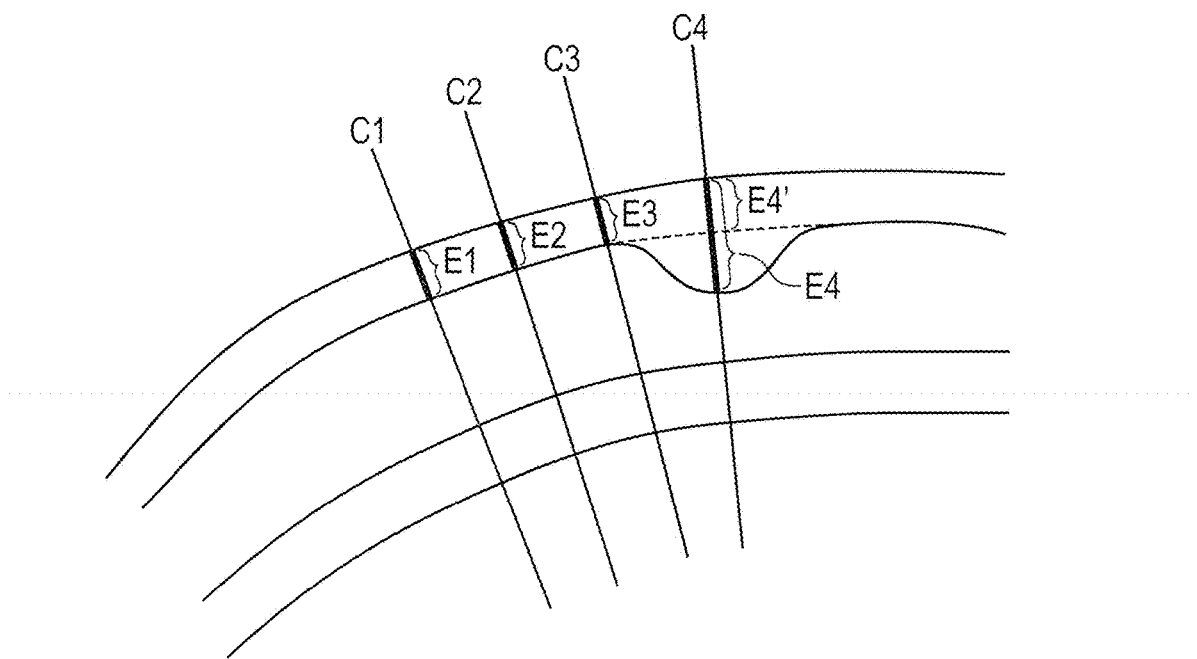
FIG. 11 is a diagram for illustrating a method of detecting an abnormality in a vessel according to this embodiment.

As described above, a trend in change of the vessel wall thicknesses can be predicted based on the information on the successive vessel wall thicknesses. FIG. 11 is an example in which a part of the vessel wall of a given vessel exhibits hypertrophy to be clogged. In FIG. 11, planes C1, C2, and C3 are respectively orthogonal to the travel of the vessel successive with pixel pitches for connecting the respective planes, and vessel wall thicknesses E1, E2, and E3 are calculated assuming that those planes are the respective cross sections. When the vessel wall thicknesses E1, E2, and E3 are successfully obtained, it is possible to predict a wall thickness E4' on a cross section C4 defined from the next connected pixels. A method for the prediction exhibits higher accuracy as the number of pieces of data becomes larger. For example, a second-order extrapolation is used when the number of pieces of known data is three points, and a third-order extrapolation is used when the number of pieces of known data is four points. In this example, the trend is predicted by the second-order extrapolation using three points as the number of order that can express a curved line to a minimum.

Subsequently, a wall thickness E4 on the cross section C4 is actually calculated against the obtained result of the prediction. In the example of FIG. 11, the vessel wall on a C4 cross section discontinuously exhibits abrupt hypertrophy, and hence the actual wall thickness E4 is larger than the predicted wall thickness E4'. A larger difference between E4 and E4' indicates that the continuity of the vessel wall is lower, and can be determined to exhibit a higher correlation with an abnormality in the vessel wall. Therefore, it is possible to detect an abnormal region and an abnormality amount of the vessel wall by obtaining the difference between E4 and E4'. In this case, a case when the wall thickness becomes larger is described as the abnormality in the vessel wall, but the abnormal region that can be detected is not limited to this mode, and also includes a case when the wall thickness becomes abruptly thinner, and a case when plaque adheres to the inner surface of the vessel wall.

As described above, through use of the intensity image data and the motion contrast data obtained by the OCT apparatus as in this embodiment, it is possible to acquire the information relating to the vessel wall of the retina and measure the wall thickness in a simplified manner. In addition, it is further possible to extract the vessel travel direction, and also possible to detect an abnormal location in the vessel in terms of shape, with the result that it is possible to provide the information on the vessel useful for diagnosis.

Other Embodiments

Embodiment(s) of the present disclosure can also be realized by a computer of a system or an apparatus that reads out and executes computer executable instructions (e.g., one or more programs) recorded on a storage medium (which may also be referred to more fully as 'non-transitory computer-readable storage medium') to perform the functions of one or more of the above-described embodiment(s) and/or that includes one or more circuits (e.g., an application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., a central processing unit (CPU), or a micro processing unit (MPU)) and may include a network of separate computers or separate processors to read out and to execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), a digital versatile disc (DVD), or a Blu-ray Disc (BD™) a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. An Optical Coherence Tomography (OCT) data processing apparatus comprising:
   a acquisition unit configured to acquire three-dimensional (3-D) OCT data of an object to be inspected;
   a generation unit configured to generate a motion contrast image based on the 3-D OCT data; and
   a detection unit configured to detect a inner surface coordinate of a vessel wall based on position information of an edge of a vessel region in the motion contrast image.

2. The OCT data processing apparatus according to claim 1, wherein the detection unit defines a cross section orthogonal to a travel direction of the vessel region, and detects the inner surface coordinate of the vessel wall in the cross section.

3. The OCT data processing apparatus according to claim 2, wherein the generation unit generates a OCT tomographic image based on the 3-D OCT data, and the detection unit defines the cross section orthogonal to the travel direction of the vessel region, and detects the outer surface coordinate of the vessel wall in the cross section.

4. The OCT data processing apparatus according to claim 3, wherein the detection unit generates a tubular vessel cross section image on the cross section, and detects the inner surface coordinate of the vessel wall in the tubular vessel cross section image.

5. The OCT data processing apparatus according to claim 4, wherein the detection unit detects the outer surface coordinate of the vessel wall in the tubular vessel cross section image.

6. The OCT data processing apparatus according to claim 2, wherein the detection unit defines a plurality of cross sections orthogonal to the travel direction of the vessel region, and detects a plurality of successive inner surface coordinate of the vessel wall.

7. The OCT data processing apparatus according to claim 1, further comprising an extraction unit configured to extract an inner surface structure of the vessel region from the motion contrast image, wherein the position information of the edge is position information of an edge of the inner surface structure.

8. The OCT data processing apparatus according to claim 1, wherein the generation unit generates an OCT tomographic image based on the 3-D OCT data, and the detection unit detects an outer surface coordinate of the vessel wall based on position information of an edge of a vessel region in the OCT tomographic image.

9. The OCT data processing apparatus according to claim 1, further comprising a designating unit configured to designate the vessel region on the motion contrast image, wherein the detection unit detects the inner surface coordinate of the designated vessel region.

10. The OCT data processing apparatus according to claim 1, wherein the acquisition unit includes a Swept Source Optical Coherence Tomography (SS-OCT) apparatus.

11. An Optical Coherence Tomography (OCT) data processing method comprising:
    acquiring three-dimensional (3-D) OCT data of an object to be inspected;
    generating a motion contrast image based on the 3-D OCT data; and
    detecting an inner surface coordinate of a vessel wall based on position information of an edge of a vessel region in the motion contrast image.

12. A non-transitory computer readable tangible medium having stored thereon a program for causing a computer to execute each step of the OCT data processing method of claim 11.

* * * * *